(12) United States Patent
Miller et al.

(10) Patent No.: US 9,044,548 B2
(45) Date of Patent: Jun. 2, 2015

(54) MEDICAL DELIVERY DEVICE HAVING AIR SHOT MEANS

(75) Inventors: Thomas Dedenroth Miller, Brønshøj (DK); Martin von Bülow, Helsingør (DK); Klaus Thøgersen, Charlottenlund (DK); Lars Mørch Groth, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 2042 days.

(21) Appl. No.: 11/449,538

(22) Filed: Jun. 8, 2006

(65) Prior Publication Data

US 2007/0016143 A1  Jan. 18, 2007

Related U.S. Application Data

(63) Continuation of application No. PCT/DK2004/000818, filed on Nov. 25, 2004.

(60) Provisional application No. 60/528,302, filed on Dec. 10, 2003.

(30) Foreign Application Priority Data

Dec. 8, 2003 (EP) ..................................... 03388085

(51) Int. Cl.
    *A61M 5/31* (2006.01)
    *A61M 5/315* (2006.01)
    *A61M 5/24* (2006.01)

(52) U.S. Cl.
    CPC ............. *A61M 5/31583* (2013.01); *A61M 5/24* (2013.01); *A61M 5/3146* (2013.01);
    (Continued)

(58) Field of Classification Search
    CPC . A61M 5/20; A61M 5/24; A61M 2005/2485; A61M 2005/2488; A61M 5/3146; A61M 5/31501; A61M 2005/31508; A61M 5/36; A61M 5/315; A61M 5/31515; A61M 5/31511; A61M 5/31513; A61M 5/31525; A61M 5/31528; A61M 5/31548; A61M 5/3155; A61M 5/31551
    USPC .................................. 604/186, 187, 208, 232
    See application file for complete search history.

(56) References Cited

U.S. PATENT DOCUMENTS 5,112,317 A * 5/1992 Michel .......................... 604/208
5,688,251 A * 11/1997 Chanoch ....................... 604/208

(Continued)

FOREIGN PATENT DOCUMENTS

| EP | 0 937 477 B1 | 11/2004 |
| WO | WO 98/10814 A1 | 3/1998 |
| WO | WO 2005/053778 A1 | 6/2005 |

OTHER PUBLICATIONS

European Search Report sent May 3, 2004 in counterpart European Patent Application No. 03388085.7.

(Continued)

*Primary Examiner* — Aarti B Berdichevsky
*Assistant Examiner* — Laura Schell
(74) *Attorney, Agent, or Firm* — Wesley A. Nicolas; Reza Green; Richard W. Bork

(57) ABSTRACT

An air shot or priming mechanism for an injection pen. The injection pen comprises a cartridge-holder and a housing. The cartridge-holder interacts with a nut-member capable of driving the piston rod forward when relatively rotated. The cartridge-holder is rotational coupled to the housing such that rotation of the cartridge-holder relatively to the housing causes the nut-member and the piston rod to rotate relatively, thus the relative angular rotation between the cartridge-holder and the housing determines the size of the air shot so performed.

7 Claims, 6 Drawing Sheets

(52) U.S. Cl.
CPC ....... *A61M 5/31535* (2013.01); *A61M 5/31541* (2013.01); *A61M 5/3155* (2013.01); *A61M 5/31551* (2013.01); *A61M 5/31585* (2013.01)

(56) References Cited

U.S. PATENT DOCUMENTS 6,004,297 A * 12/1999 Steenfeldt-Jensen et al. ............................ 604/207

2007/0142789 A1 * 6/2007 Fisher et al. .................. 604/207

OTHER PUBLICATIONS

International Preliminary Examination Report sent Jun. 22, 2006 in counterpart PCT Application No. PCT/DK2004/000818.
Chinese Office Action sent Jun. 27, 2008 in counterpart Chinese Application No. 200480036486.9.
Chinese Office Action sent Jun. 5, 2009 in counterpart Chinese Application No. 200480036486.9.

* cited by examiner

MEDICAL DELIVERY DEVICE HAVING AIR SHOT MEANS

CROSS-REFERENCE TO RELATED APPLICATIONS

This application is a continuation of International Application Number PCT/DK2004/000818, filed Nov. 25, 2004, which claims priority to European Patent Application Number 03388085.7, filed Dec. 8, 2003, and U.S. Provisional Application Ser. No. 60/528,302, filed Dec. 10, 2003, the contents of each of which is incorporated herein in its entirety.

THE TECHNICAL FIELD OF THE INVENTION

The invention relates to a medical delivery device by which medicine may be apportioned in preset doses from a cartridge. The invention especially relates to an air shot mechanism for such medical delivery device.

DESCRIPTION OF RELATED ART

Some medication such as insulin is self-administered. The typical diabetes patient will require injections of insulin several times a day.

Medication delivery device have been developed to facilitate the self-administration of medication. The typical medication delivery device includes a cartridge-holder into which a cartridge containing insulin or other medication is loaded.

The medical delivery device can either be a durable delivery device having an exchangeable cartridge or it can be a prefilled delivery device having an encapsulated cartridge.

The cartridge-holder is an elongated structure with proximal and distal ends. The distal end of the cartridge-holder includes means for engaging a double-ended needle assembly. The double-ended needle assembly pierces an elastomeric seal in the distal end of the cartridge such that an end of the needle assembly enters the cartridge.

The proximal end of the cartridge is closed of by a slidable plunger such that the content of the cartridge can be pressed out through the needle assembly when the plunger is moved towards the distal end of the cartridge.

When a user wants to self-administer a dose of medicament, a cartridge is loaded into the medical delivery device and a double-ended needle is mounted on the distal end of the device. The user then selects a dose and operates the medical delivery device to urge the plunger distally to deliver the selected dose.

The double-ended needle mounted on the medical delivery device contains air in the interior lumen and if the user leaves the double-ended needle on the medical delivery device for a longer period of time air can be sucked into the cartridge e.g. due to temperature variations. It is therefore recommendable to ensure that both the double-ended needle assembly and the cartridge are emptied for air before a dose is set and injected.

To get rid of possible air a small dose of medicine is set and an injection operation is made without insertion of the double-ended needle into the skin. By this so called air shot, air is driven out through the double-ended needle. At the point of the double-ended needle it can easily be seen if all air has been expelled. If a fine liquid jet is not seen at the end of the air shot a new small dose must be set and a new air shot be made until such a jet is seen.

To avoid having to perform repetitive settings of a small dose and subsequent air shots, the user may feel an impulse to set a somewhat larger dose to make sure only one air shot has to be made. This has lead to the development of medical delivery devices having a separate air shot button by which a predetermined amount can be expelled.

Such medical delivery devices are disclosed in WO 98/10814 and EP 937 477.

The medical delivery devices so disclosed has a separate air shot button formed as a ring or collar surrounding the housing of the device. The ring interfaces with a nut member inside the housing. When rotating the ring, the nut member rotates with it and drives forward the piston rod.

It is however rather cumbersome for people to rotate this relatively small ring. This is particular difficult for people having impaired sight or reduced motor skills which are often the case with people suffering from diabetes.

It is also a drawback that the ring, as disclosed in WO 98/10814, is left unprotected when the cap is not mounted such that it can be accidentally operated if the medical delivery device is left unattended with the double-ended needle mounted on the medical delivery device e.g. if the medical delivery device is left laying on a table. The medical delivery device could e.g. roll by it self on a sloping surface and expel expensive medicine.

DESCRIPTION OF THE INVENTION

In order to avoid these drawbacks, the cartridge-holder itself is according to the present invention used as a mean for performing an air shot.

The cartridge-holder is due to its size easy gripable and is usually covered by a cap when the device is not used.

When a user wants to perform an air-shot, the user rotates the cartridge-holder relatively to the housing. Since the cartridge-holder is operational coupled to the piston rod drive which comprises the piston rod guide and the nut-member, one of these parts are rotated relatively to the other when the cartridge-holder or the housing is rotated.

The relative rotation between the piston rod guide and the nut-member will cause the piston rod to be moved forward.

The relative rotational movement between the cartridge-holder and the housing is in a preferred embodiment defined by a limiter on the housing being movable relatively to an opening provided in the cartridge-holder.

The location of the limiter and the opening is not in anyway bound, the limiter could be provided either on the housing or on the cartridge-holder and the opening vice versa. Which one is moved is indifferent, what counts is the relative movement between the opening and the limiter.

The nut-member is provided with a distal part and a proximal part which parts carries a number of ratchet pawls. The distal ratchet pawls interface a ratchet on the interior of the cartridge-holder whereas the proximal pawls interface a ratchet on the interior of the housing.

Now when rotating the cartridge-holder in a first direction the distal ratchet pawls slides over the ratchet on the interior of the cartridge-holder whereas the proximal pawls are locked by the ratchet on the interior of the housing thereby preventing the nut-member from rotating.

When rotating back the cartridge-holder in an opposite rotational direction, the nut-member do follow the rotation and since the piston rod is rotational locked, it will be screwed forward by the rotation of the nut-member.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Initially it may be convenient to define that, the term "distal end" of the injection device 1 is meant to refer to the end carrying the injection needle, whereas the "proximal end" is meant to refer to the opposite end carrying the injection button 35. When the term "distal end" are used for other parts of the injection device 1, it is meant to refer to the end pointing towards the distal needle carrying end of the injection device 1, whereas the term "proximal end" refer to the end pointing towards the proximal end of the injection device 1.

Figure 1:
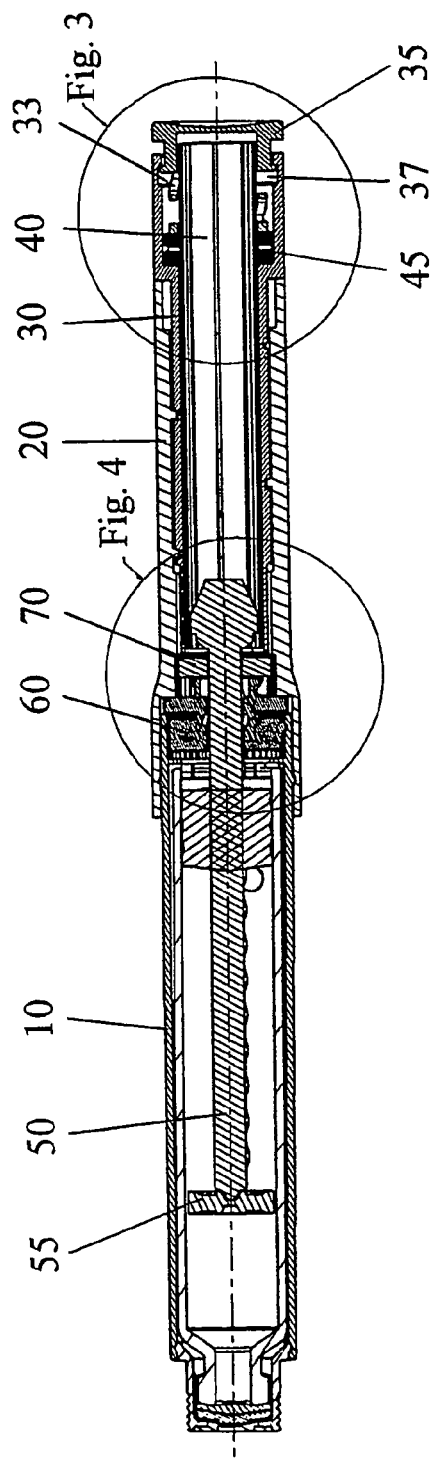
FIG. 1 Shows a cross-sectional view of the delivery device according to the invention.
Figure 2:
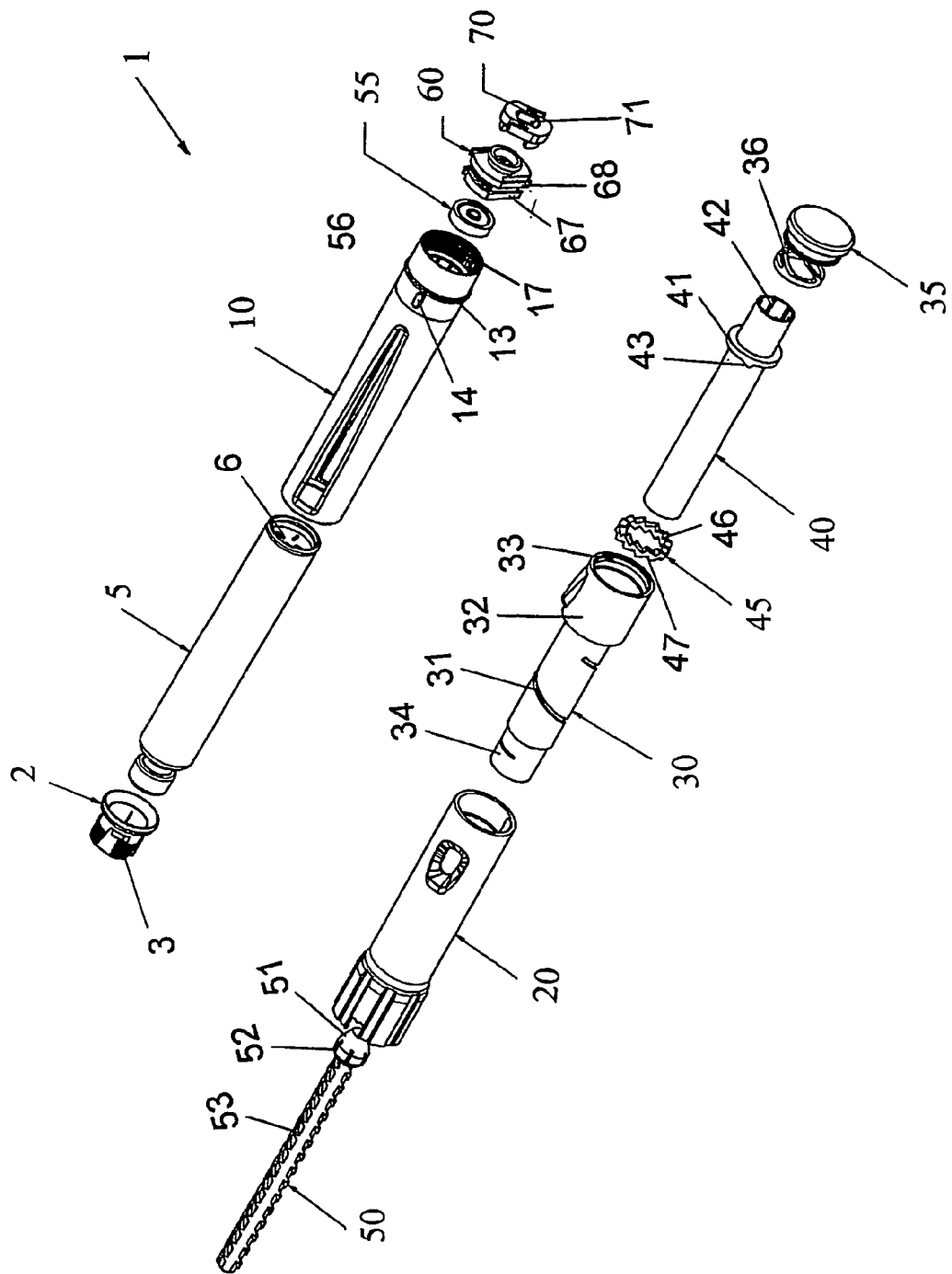
FIG. 2 Shows an exploded perspective view of the delivery device according to the invention.

FIGS. 1 and 2 discloses the injection device 1 according to the invention. Exterior the injection device 1 comprises a cartridge-holder 10 coupled to the distal end of a housing 20. The housing 20 comprises the dose setting and injection mechanism.

A scale drum 30 is in its outer wall provided with a helical track 31 which is engaged by a helical rib 21 along the inner wall of the housing 20. At its proximal end the scale drum 30 has a diameter exceeding the inner diameter of the housing 20 to form a dose setting button 32 which on its cylindrical outer wall is knurled to ensure a good finger grip.

A piston rod guide 40 having a flange 41 near the proximal end and having a number of longitudinal fins 42 provided at its inner sidewall fits into the scale drum 30.

The piston rod 50 has at its proximal end a knob 51 having an outer diameter larger than the diameter of the piston rod 50 which knob 51 fits into the piston rod guide 40. The knob 51 has a number of longitudinal slots 52 into which slots 52 the fins 42 on the piston rod guide 40 fits such that the piston rod 50 and the piston rod guide 40 is coupled to each other so that rotation but not longitudinal displacement is transmitted between the two elements. The piston rod 50 is further provided with a non circular cross section and an outer thread 53

The piston rod guide 40 is coupled to the scale drum 30 through a dish 45 having ratchet teeth both at its proximal side 46 and at its distal side 47. One or more piston rod guide pawls 43 provided on the flange 41 of the piston rod guide 40 interfaces with the teeth of the dish 45 on the proximal side 46. The teeth provided on the distal side 47 of the dish 45 interfaces a ratchet provided in the scale drum 30.

Figure 3:
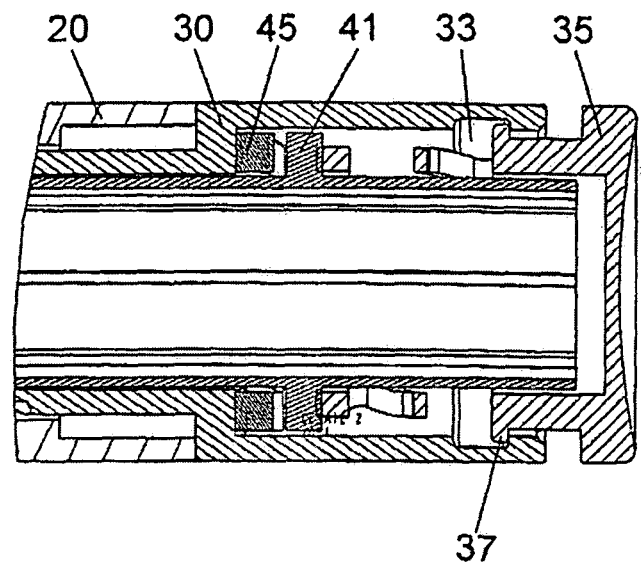
FIG. 3 Shows a detailed cross-sectional view of the dose setting mechanism according to an embodiment of the invention.

The scale drum 30 is at the most proximal end provided with an injection button 35. The injection button 35 shown in details in FIG. 3 is rotatable secured in the scale drum 30 by having a ring shaped projection 37 inserted into a ring shaped channel 33 on the inside surface of the scale drum 30. A resilient part 36 urges the proximal surface of the flange 41 of the piston rod guide 40 towards the dish 45 and the not shown ratchet at the proximal end of the scale drum 30.

The scale drum 30 is further provided with a number of slits 34 such that the distal area of the scale drum 30 can be forced outward in a peripheral direction when the knob 51 of the piston rod 50 enters the distal end of the scale drum. The function of this will be explained later.

In the distal end of the injection device 1 a needle holder 2 is secured to the cartridge-holder 10. The needle holder 2 has a thread 3 or similar fastening mean onto which a not shown injection needle can be fastened. The needle holder 2 and the cartridge-holder 10 could alternatively be moulded as one unit.

A cartridge 5 containing a fluid medicament is provided inside the cartridge-holder 10. The cartridge 5 has an open proximal end which is sealed by a rubber piston 6. By forcing the rubber piston 6 in the distal direction, the fluid medicament in the cartridge 5 can be pressed out through the not shown injection needle fastened to the distal end of the injection device 1. The injection needles most commonly used are doubled pointed injection needles having a fore-needle for penetrating the skin of a user and a back-needle for penetrating a not shown rubber membrane at the distal end of the cartridge 5.

The cartridge 5 can be either replaceable or it can be permanently encapsulated in the injection device 1.

A nut member 60 is provided in the junction between the cartridge-holder 10 and the housing 20 which nut member 60 has an inner thread 63 corresponding to the outer thread 53 of the piston rod 50. When the piston rod 50 is rotated relatively to the nut member 60, the piston rod 50 is screwed forward further into the cartridge 5.

A pressure foot 55 is located between the piston rod 50 and the rubber piston 6. The pressure foot 55 is preferably provided with a peripheral ring 56 on both sides such that the force from the forward movement of the piston rod 50 is transmitted to the rubber piston 6 at the periphery of the rubber piston 6.

Further a one-way coupling 70 is provided. This one-way coupling 70 has a hole 71 which mates the not circular cross section of the piston rod 50 to allow axially displacement but not rotation of the piston rod 50 in relation to the one-way coupling 70. On the exterior the one-way coupling 70 is provided with pawls 72 which interfaces a first ratchet 22 on the inside surface of the housing 20, such that the one-way coupling 70 can be rotated relatively to the housing 20 in one direction but not in the opposite direction. The allowed rotational direction being the one that screws the piston rod 50 forward in the tread 63 of the nut member 60 preventing backwards movement of the piston rod 50. During injection, the one-way coupling 70 will henceforth be free to rotate in the ratchet 22 of the housing 20.

When a dose is set by rotating the dose setting button 32 in a clockwise direction, the scale drum 30 is screwed out of the housing 20 and the dose setting button 32 together with the injection button 35 is lifted away from the proximal end of the housing 20. The piston rod guide 40 is kept non-rotational due to its coupling to the piston rod 50 which again is prevented from rotation by the one-way coupling 70 interfacing the housing 20. If a dose is reduced by rotating the dose setting button 32 in an anticlockwise direction the pawl mechanism 72, 22 between the one-way coupling 80 and the housing 20 is sufficient reluctant to rotate in its not blocking direction to prevent the piston rod guide 40 from following this anticlockwise rotation.

As the scale drum 30 is screwed out of the housing 20, the not shown pawl teeth of the scale drum 30 rides over the pawl teeth on the distal side 47 of the dish 45 thereby making a clicking sound e.g. indicating the number of doses being set.

When injecting the set dose, the injection button 35 is pushed back in the distal direction towards the housing 20. During this movement the scale drum 30 rotates in the anti clock wise direction. The pressure applied to the injection button 35 forces the piston rod guide pawls 43 on the flange 41 to engage the pawl teeth on the proximal side 46 of the dish 45. Both this engagement and the engagement between the not shown pawl teeth provided on the interior of the proximal end of the scale drum 30 and the pawl teeth on the distal side 47 of the dish 45 is non rotational when the scale drum 30 is rotated in the anti clockwise direction. Due to this the piston rod guide 40 is rotated with the scale drum 30. This rotation forces the piston rod 50 to rotate due to the coupling 42, 52 between the piston rod guide 40 and the piston rod 50. As the piston rod 50 is rotated, it is screwed out of the inner thread 63 of the nut member 60 and further into cartridge 5 located in the cartridge holder 10. This forward movement of the piston rod 50 moves the rubber piston 6 inside the cartridge 5 and expels the fluid medicament confined in the cartridge 5 out of the not shown injection needle mounted to the needle holder 2.

Figure 4:
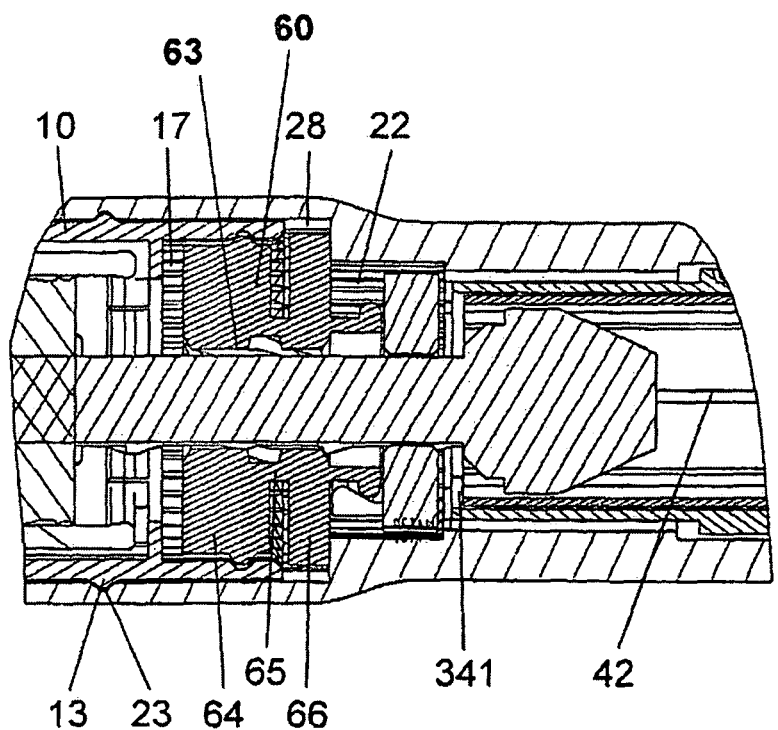
FIG. 4 Shows a detailed cross-sectional view of the air shot mechanism according to an embodiment of the invention.
Figure 5:
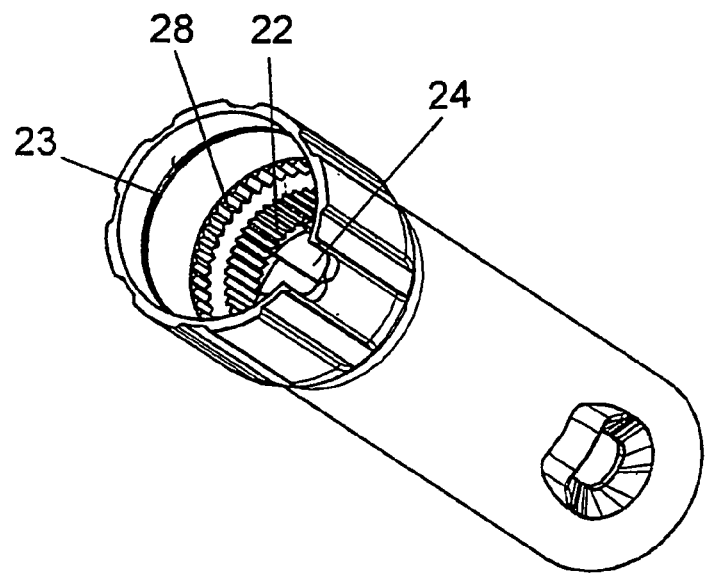
FIG. 5 shows a perspective view of the housing according to an embodiment of the invention.
Figure 6:
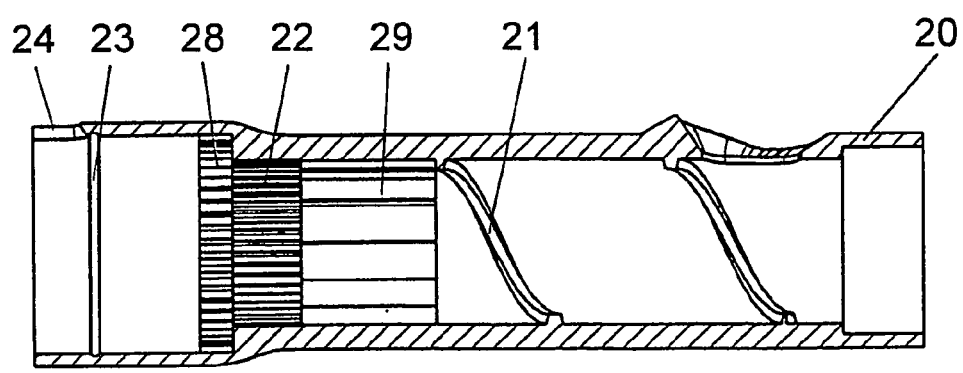
FIG. 6 shows a cross-sectional view of the housing according to an embodiment of the invention.

The one-way coupling 70 is coupled to the neighbouring nut member 60 through a click-on connection which is best seen in FIG. 4.

The nut member 60 comprises two parts, a distal part 64 and a proximal part 66 which are connected through an intermediate part 65. These three parts 64, 65, 66 are preferably moulded as one part—the nut member 60.

The distal part 64 of the nut member 60 has on its periphery a number of distal ratchet pawls 67 interacting with a cartridge holder ratchet 17 provided on the interior of the cartridge holder 10.

The proximal part 66 of the nut member 60 has on its periphery a number of proximal ratchet pawls 68 interacting with a second ratchet 28 provided on the interior of the housing 20.

The cartridge holder 10 is connected to the housing 20 in a way allowing rotation. The cartridge holder 10 is at its proximal end provided with a circular protrusion 13 located on the exterior surface. This circular protrusion 13 engages a circular groove 23 provided in the interior of the housings 20 distal end. The circular protrusion 13 is able to rotate within the groove 23. A limiter 14 in the shape of a protrusion on the exterior of the cartridge holder 10 moves within an opening 24 in the housing 20 during rotation such that the angular size of the opening 24 defines the angle that the cartridge holder 10 can be moved relatively to the housing 20.

When the piston rod 50 has pushed the pressure foot 55 and the rubber piston 6 to the distal end of the cartridge 5 and the cartridge 5 is about to be empty, the knob 51 on the piston rod 50 enters the distal area of the scale drum 30. When setting up a dose, the scale drum 30 will be moved in the proximal direction relatively to the knob 51 on the piston rod 50. When the knob 51 is in the end of the distal area of the scale drum 30, the peripheral area of the distal end of the scale drum will be pressed outward due to the diameter difference between the knob 51 and the inside diameter of the distal area of the scale drum 30. The slits 34 facilitate this peripheral movement. The housing 20 is on the inside provided with a end-of-content ratchet 34 which will be engaged by the peripheral part of the distal area of the scale drum 30 during its outward movement thereby preventing further movement of the scale drum 30 in the proximal direction. This locking of the scale drum 30 is coordinated with the content of the cartridge 5 such that the mechanism prevents the user for dialling up a dose larger than the content remaining in the cartridge 5. The distal end of piston rod guide 40 and/or the distal area of the scale drum 30 must be configured to enable the peripheral movement of the distal area of the scale drum 30, e.g. by providing the scale drum 30 with inwardly pointing protrusions 341 which will force the distal area of the scale drum 30 in the peripheral direction when encountering the conical distal part of the knob 51 as best seen in FIG. 4.

When performing an air shot the user rotates the cartridge holder 10 in the anti clockwise direction and the cartridge holder distal ratchet 17 on the cartridge holder 10 will ride over the distal pawls 67 on the nut member 60. The proximal pawls 68 on the nut member 60 engages the second ratchet 28 of the housing 20 in a way preventing rotational movement between the housing 20 and the nut member 60. After a certain angular rotation of the cartridge-holder 10, the limiter 14 will engage the side of the opening 24 and thereby prevent further rotation.

Following this, the user rotates the cartridge holder 10 back in the clockwise direction until the limiter 14 engages the opposite side of the opening 24. During this rotation, the cartridge holder ratchet 17 will engage the distal ratchet pawls 67 on the nut member 60 and rotate the nut member 60 in the anti clock wise direction. Further, the proximal pawls 68 on the nut member 60 are free to rotate in the ratchet 28. The pawls 72 on the one-way coupling 70 engages the ratchet 22 on the interior of the housing thereby preventing the one-way coupling 70 from rotating inside the housing 20

Since the nut member is rotated relatively to the piston rod 50 which is rotational locked by the one-way coupling 70, the piston rod 50 is moved towards the distal end of the cartridge holder 10 moving the rubber piston 6 inside the cartridge 5 forward in the distal direction if a cartridge 5 is inserted in the device 1

Figure 7:
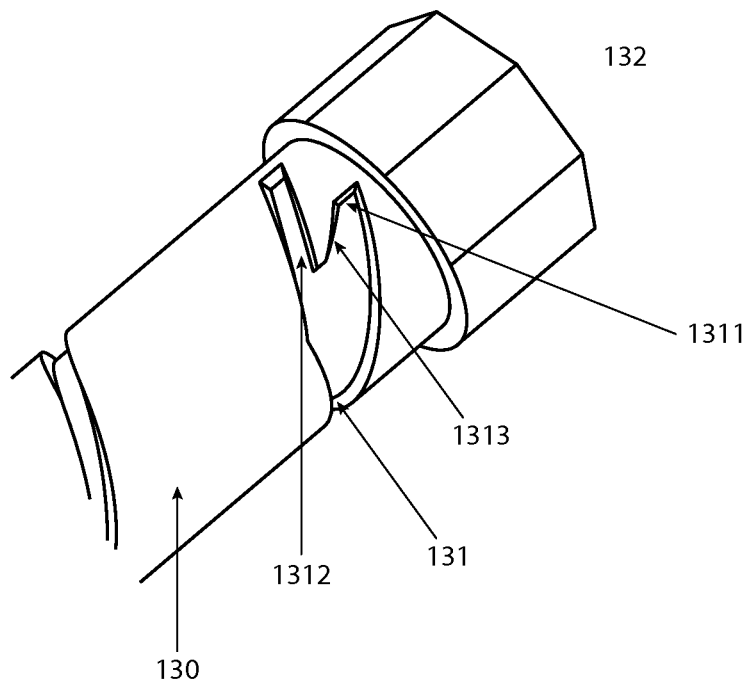
FIG. 7 shows a perspective view of the scale drum according to an embodiment of the invention.
Figure 8:
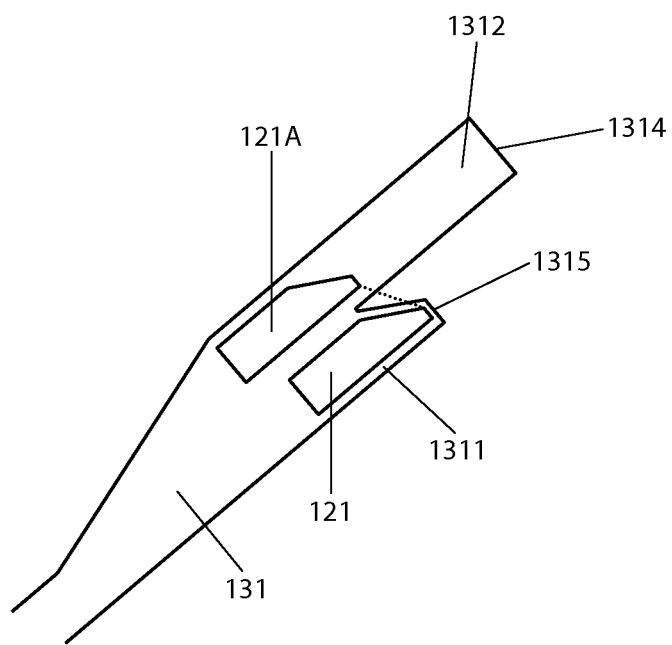
FIG. 8 shows a view of the lay-out of the tracks of the scale drum in FIG. 7

Another air shot mechanism is disclosed on FIGS. 7 and 8. The scale drum 130 is provide with a helical track 131 At the proximal end of the scale drum 130, the helical track 131 is divided in to primary track 1311 and a secondary track 1312.

In usual operation when a dose is being set or expelled, the helical rib 121 of the housing 20 is guided in the helical track 131 and the primary track 1311.

When an air shot is set, the user pulls the knob 132 of the scale drum 130 in the proximal direction away from the housing 20. This movement forces the helical rib 121 into the secondary track 1312 by sliding on the sidewall 1312 of the primary track 1311. This new position is indicated by 121A.

The dose setting button 132 will now be in a position where it protrudes from the proximal end of the housing 20. In order to release the predetermined air shot the user must push back the dose setting button 132 to its original position. Doing so, the thread 121A will abut the end surface 1314 of the secondary track 1312 in stead of the end surface of the primary track. This movement will release a dose due to the supplementary rotation of the scale drum 130. The predetermined dose of this air shot dose is decided by the difference in the angular position of the two end surfaces 1314, 1315 of the primary track 1311 and the secondary track 1311.

Figure 9:
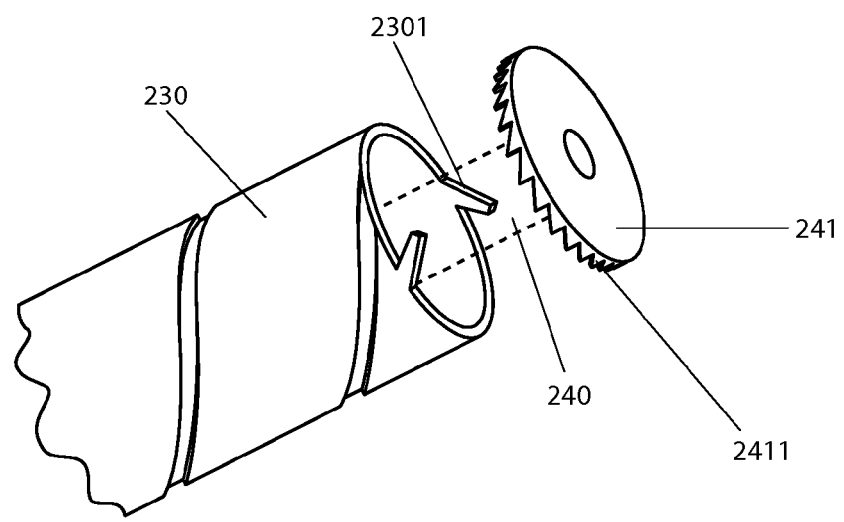
FIG. 9 shows a perspective view of the scale drum according to yet an embodiment.

Yet another embodiment is disclosed in FIG. 9. In this embodiment the zero point on the scale drum 230 will be located more towards the distal end of the scale drum 230 than normal. The result being that the proximal part of the scale drum 230 carrying the dose setting button will protrude from the proximal end of the housing when the number zero is present in the window in the housing. In order to ensure this position a spring urging the scale drum in the proximal direction can be present.

When an air-shot is made, the scale drum 230 is simply screwed in the anti clockwise direction moving the scale drum 230 in the distal direction in the housing. As the proximal end of the scale drum 230 is provided with a number of ratchet teeth 2301 interfacing a number of opposite directed ratchet teeth 2411 provided on a flange 241 on the piston rod guide 240, the piston rod guide 240 will be forced to follow the rotation of the scale drum 230. When the scale drum is returned to the zero position after the air-shot, the ratchet teeth 2301 on the scale drum 230 will override the ratchet teeth on the flange 241 of the piston rod guide 240. Once the scale drum 230 has returned to its zero position, the user can perform another air-shot by rotating the scale drum in the anti clockwise direction or the user can set a desired dose by rotating the scale drum in the clockwise direction.

Some preferred embodiments have been shown in the foregoing, but it should be stressed that the invention is not limited to these, but may be embodied in other ways within the subject matter defined in the following claims.

LISTING OF PARTS

1 Injection Device
  2 Needle Holder
  3 Thread
5 Cartridge
  6 Rubber Piston
10 Cartridge Holder
  13 Circular Protrusion
  14 Limiter
  17 Cartridge Holder Ratchet
20 Housing
  21 Helical Rib
  22 First Ratchet
  23 Circular Groove
  24 Opening
  28 Second Ratchet
30 Scale Drum
  31 Helical Track
  32 Dose Setting Button
  33 Ring Shaped Channel
  34 end-of-content ratchet
    341 inwardly pointing protrusion
35 Injection Button
  36 Resilient Part
  37 Ring Shaped Projection
40 Piston Rod Guide
  41 Flange
  42 Longitudinal Fins
  43 Piston rod guide Pawls
45 Dish
  46 Proximal Side
  47 Distal Side
50 Piston Rod
  51 Knob
  52 Longitudinal slots
  53 Outer Thread
55 Pressure Foot
  56 Peripheral Ring
60 Nut Member
  63 Inner Thread
  64 Distal Part
  65 Intermediate Part
  66 Proximal Part
  67 Distal Ratchet Pawls
  68 Proximal Ratchet Pawls
70 One-way Coupling
  71 Hole
  72 Pawls
121 Helical Rib
121A New Position of Helical Rib
130 Scale Drum
  131 Helical Track
  132 Dose Setting Button
  1311 Primary Track
  1312 Secondary Track
  1313 Side Wall
  1314 End Wall of Primary Track
  1315 End Wall of Secondary Track
230 Scale Drum
  2301 Scale drum ratchet teeth
240 Piston rod guide
  241 Flange
  2411 Flange ratchet teeth

The invention claimed is:

1. A delivery device for delivering a fluid medicament, comprising:
A cartridge-holder for supporting a cartridge containing the fluid medicament to be delivered,
A housing having the cartridge-holder coupled to a distal end, the housing further comprising:
A piston rod having an outer thread, and
A piston rod drive to drive the piston rod in a longitudinal direction comprising:
A piston rod guide engaging the piston rod to allow axial displacement but not rotation of the piston rod in relation to the piston rod guide, and
A nut member which is not longitudinally displaceable in the housing having an inner thread mating the thread of the piston rod,
wherein rotation of the piston rod guide and the nut member relatively to each other drives the piston rod in the longitudinal direction, and
wherein the cartridge-holder is connected to the housing in a way allowing rotation and operationally coupled to the piston rod drive such that when the cartridge-holder and the housing are rotated relative to each other without axial displacement, the piston rod guide or the nut member are rotated whereby the piston rod is driven in the longitudinal and distal direction in order to expel a predetermined air shot dose, and wherein the relative rotational movement between the cartridge-holder and the housing is limited such that the size of the air-shot dose is predetermined by this limitation.

2. A delivery device for delivering a fluid medicament according to claim 1, wherein the housing is provided with an opening and the cartridge-holder is provided with a limiter such that the movement of the limiter in the opening defines the possible angular movement between the cartridge-holder and the housing.

3. A delivery device for delivering a fluid medicament according to claim 2, wherein the nut-member comprises a distal part carrying a number of distal ratchet pawls and a proximal part carrying a number of proximal ratchet pawls, the distal part and the proximal part being connected by an intermediate part.

4. A delivery device for delivering a fluid medicament according to claim 3, wherein the distal ratchet pawls interfaces a cartridge holder ratchet provided on the interior surface of the cartridge holder.

5. A delivery device for delivering a fluid medicament according to claim 4, wherein the proximal ratchet pawls interfaces a second ratchet provided on the interior surface of the housing.

6. A delivery device for delivering a fluid medicament according to claim 5, wherein the cartridge holder ratchet slides over the distal ratchet pawls when the cartridge holder is rotated in a first direction and that the cartridge holder ratchet engages the distal ratchet pawls when the cartridge holder is rotated in a second opposite direction.

7. A delivery device for delivering a fluid medicament according to claim 6, wherein the engagement between the cartridge holder ratchet and the distal ratchet pawls rotates the nut member simultaneously with the rotation of the cartridge holder and that the piston rod is rotational locked to the housing through a one-way coupling.

* * * * *